United States Patent [19]

MacWinnie et al.

[11] Patent Number: 5,441,534

[45] Date of Patent: * Aug. 15, 1995

[54] HEAT PACK FOR THERMAL TREATMENT OF BREAST

[76] Inventors: Virginia MacWinnie; John V. MacWhinnie, both of R.R. 519 Deerfield Rd., Water Mill, N.Y. 11976

[*] Notice: The portion of the term of this patent subsequent to Apr. 19, 2011 has been disclaimed.

[21] Appl. No.: 15,213

[22] Filed: Feb. 9, 1993

[51] Int. Cl.$^6$ ............................................. A61F 7/00
[52] U.S. Cl. ............................... 607/108; 383/901
[58] Field of Search ............ 128/379, 380, 399–402; 604/294, 303–304; 383/901, 907; 607/96, 104, 108, 114

[56] References Cited

U.S. PATENT DOCUMENTS

| | | | |
|---|---|---|---|
| 14,024 | 11/1915 | Whitmarsh. | |
| 2,049,723 | 8/1936 | Pomperanz | 128/402 |
| 2,298,361 | 10/1942 | Freund | 150/2.2 |
| 2,853,077 | 9/1958 | Hunau | 128/493 |
| 2,897,821 | 8/1959 | Lerner | 128/479 |
| 3,430,632 | 3/1969 | James et al. | 128/425 |
| 3,500,832 | 3/1970 | Nunnery | 128/379 |
| 3,780,537 | 12/1973 | Spencer | 62/530 |
| 3,830,676 | 8/1974 | Elkins | 128/403 |
| 3,993,621 | 12/1976 | Fletcher et al. | 128/2 H |
| 4,094,773 | 8/1977 | Baldwin, III | 128/402 |
| 4,416,281 | 11/1983 | Cooper et al. | 128/402 |
| 4,552,149 | 11/1985 | Tatsuki | 128/402 |
| 4,846,176 | 1/1989 | Golden | 128/400 |
| 5,050,595 | 9/1991 | Krafft | 128/379 |
| 5,133,348 | 7/1992 | Mayn | 128/402 |
| 5,304,215 | 4/1994 | MacWhinnie et al. | 607/106 |

*Primary Examiner*—Lee S. Cohen
*Assistant Examiner*—John P. Lacyk
*Attorney, Agent, or Firm*—Alfred M. Walker

[57] ABSTRACT

The present invention relates to a thermal heat pack for heating the female breast during post partum nursing and, more particularly, to a thermal heat pack which readily conforms to the contours of different sized female breasts to provide therapeutic heat to an adjacent breast to reduce swelling and irritation. The present invention overcomes the disadvantages of the prior art by providing a bendable thermal heat unit which assumes a cup or cone shape upon application to the breast. The present invention adjusts and conforms to various sizes of the female breasts to which it is to be applied. The present invention provides a layered conformable member with a shape substantially like a disk having selected indentations to permit formation of various sized rounded conical cups.

17 Claims, 7 Drawing Sheets form to various sized female breasts.
HEAT PACK FOR THERMAL TREATMENT OF BREAST

BACKGROUND OF THE INVENTION

The present invention relates to a thermal heat pack for heating the female breast during post partum nursing and, more particularly, to a thermal heat pack which readily conforms to the contours of different sized female breasts to provide therapeutic heat to an adjacent breast to reduce swelling and irritation.

A number of cup shaped thermal heat packs are known in the prior art in which thermal heat is provided through a heat pack to provide a therapeutic heat to the human body. Examples of this type of heat pack are shown in U.S. Pat. Nos. Re 14,024 of Whitmarsh, 2,298,361 of Freund, 3,500,832 of Nunnery, and 5,050,595 of Krafft. Moreover, U.S. Pat. No. 3,995,621 of Fletcher discloses a liquid cooled brassiere used with diagnostic mammography. Other brassiere patents in general are disclosed in U.S. Pat. Nos. 2,853,077 of Hunau and 3,430,632 of James. Heat packs in general are disclosed in U.S. Pat. Nos. 3,780,537 of Spencer and 4,846,176 of Golden. Furthermore, U.S. Pat. No. 3,897,821 of Lerner describes a swimming garment wherein breast shaped cups are formed from flat sheets having V-shaped cuts in the sheets.

These patents are incorporated by reference herein for teaching devices in which breast shaped cups are provided for therapeutic use or otherwise.

The above prior art devices have many disadvantages. Typically the devices include cup shaped portions which do not conform closely to various sizes of the breast. If the heat pack does not snugly fit the breast once in position, the heat pack may be too tight or too loose to optimize heating resulting in uneven application of heat to the breast.

The present invention overcomes the disadvantages of the prior art by providing a bendable thermal heat unit which assumes a cup or cone shape upon application to the breast. The present invention adjusts and conforms to various sizes of the female breasts to which it is to be applied. The present invention provides a layered conformable member with a shape substantially like a disk having selected indentations to permit formation of various sized rounded conical cups.

Although the Freund, Nunnery and Krafft prior art thermal pack units provide cup shaped heat packs, the prior art devices do not increase or decrease in size to accommodate, adjust or conform to various sized breasts. With all of the prior art, it is necessary to provide various sizes of specific heat packs to include the wide range of female breast sizes. Consequently, a large variety of different sizes must be provided so that a user can select a size which will fit a particular breast. With the present adjustable invention, however, one size fits all.

The present invention overcomes the disadvantages of the prior art and provides a simple, pliable, lightweight thermal heat pack which readily conforms to the contours of any sized female breast to provide therapeutic heat or cold to the adjacent breast areas.

BRIEF SUMMARY OF THE INVENTION

The present invention provides a thermal pack capable of supplying hot or cold temperatures. The thermal pack readily adjusts and conforms to the contours of various sized female breasts to therapeutically heat or cool adjacent skin areas of the breast. The thermal pack has a conforming member which is substantially disk shaped or cylindrical and which has an internal cavity for containing a heat retentive and conductive material.

In the alternative, the thermal pack has a conforming member which is disk-shaped or cylindrical, but which is constituted from a pliant gelatinous material which retains a flexible three dimensional shape when cut.

The heat retaining heat conductive material is flexible, preferably a gel which can be primarily liquid in nature or primarily solid in nature, and which, due to its flexibility as a gel, can be adapted to conform to any sized contour of the female breast. Heat retentive heat conductive gels are conventional and are well known in the art of medical thermal pack appliances.

The heat conductive material may conduct heat either toward the breast skin surface, wherein the breast is warmed, or may conduct heat away from the breast skin surface, wherein the breast is cooled.

Further, the substantially disk-shaped centrally located conformable member is provided with selectively positioned indentations to permit the disk in its non-use flattened form to flex mechanically and thus to assume a cup shape when put into use. In this manner the disk-shaped conformable member is able to adjust and con- The indentations which permit the mechanical flexing of the disk-shaped conformable member are cuts made into the outer side of the disk-shaped conformable member, which outer side assumes a generally convex shape when the disk-shaped conformable member is applied to a female breast. In contrast, when the conformable member is applied to a female breast, the inner side of the conformable member assumes a generally concave shape.

Alternatively, the indentations may be made into the inner side of the disk-shaped conformable member, which inner side assumes a generally concave shape when the disk-shaped conformable member is applied to a female breast.

The indentations begin at the outer or inner side and extend generally into the disk-shaped conformable member without extending all the way therethrough. The relative depth of the indentations may vary, depending upon the nature, strength and natural flexibility of the un-indented material selected for use in constructing the disk-shaped conformable member. The more naturally flexible the material selected, the shallower may be the indentations. Conversely, where a material for the disk-shaped conformable member is relatively less flexible, the indentations will have to be made deeper, which means that the indentations will have to more closely approximate a cut which would run completely through the disk-shaped conformable member from the outer side to the inner side, or from the inner side to the outer side.

The indentations may have a rectangular cross section or an angular cross section. Although the angular cross section is preferred, either the rectangular or the angular cross section indentations will perform satisfactorily.

The rectangular cross section indentation is relatively narrow, meaning that its width is relatively small compared with its length. The rectangular cross section indentation substantially comprises a rectangular bore, the length of the rectangle being substantially perpendicular to the outer side of the disk-shaped conformable member.

The angular cross section indentation, like the rectangular cross section indentation, comprises a bore substantially perpendicular to the outer side of the disk-shaped conformable member. However, unlike the rectangular cross section indentation, the angular cross section indentation is comprised of a notch-shaped cut wherein the sides of the notch are at about a right angle in relation to each other.

The angular and rectangular cross sections for the selectively positioned indentations are merely exemplary of types of indentations which permit curved flexing of a surface. Those skilled in the art will appreciate that many varieties of indentation, scoring, notching or otherwise providing for material movement of a flat surface to permit such surface to form a cup shape will be effective in making and using the present invention.

The selectively positioned indentations may be applied to the disk-shaped conformable member in accordance with the foregoing and may be positioned in a variety of effective patterns. One such pattern of indentations comprises a plurality of such indentations with a configuration which, when viewed from above the outer or inner side of the disk-shaped conformable member has an L-shape. The plurality of L-shaped indentations would be randomly distributed over the outer side of the disk-shaped conformable member, spaced substantially equidistantly apart.

Another configuration for the indentations is a pattern in which a single elongated indentation describes substantially a spiral shape when viewed from above the outer or inner side of the disk-shaped conformable member.

Another configuration for the indentations is a pattern in which a plurality of elongated indentations comprise substantially concentric circles when viewed from above the outer or inner side of the disk-shaped conformable member.

Another configuration for the indentations is a pattern in which a plurality of elongated indentations are each substantially straight lines outwardly radiating from the about the center of the disk-shaped conformable member, each such straight elongated indentation describing a radius of the disk.

A further, and different embodiment, not preferred in the present invention but nonetheless effective and useful in practice, is a substantially square conformable member, with all of the herein described characteristics of the disk-shaped conformable member, except that the square conformable member is provided with a plurality of cuts through from its outer side to its inner side to permit flexible conformity of the surface to the female breast. The through cuts comprise substantially tapered apertures which radiate from about the center of the square conformable member to its edges. The apertures taper from a wide end at the edge of the square conformable member to a narrow end near the center of the square conformable member. In all other respects, the square conformable member shares the characteristics of the disk-shaped conformable member herein described.

Further, the thermal pack may provide a moist heat conductive foundation surface, such as terry cloth, separating the conforming member from the breast. The terry cloth or other heat conductive foundation is moistened with water when use to heat the breast but not when used to cool the breast. The water-permeated terry cloth, disposed between the breast skin and the conforming member, serves to conduct heat from the surface of the conforming member toward the breast. The heat source is the heat retentive heat conducting gel housed within a cavity in the conforming member.

In another embodiment, the thermal heat pack may have no attached moist heat conductive surface, but rather may be insertable within a separate moist heat conductive ferrule sheath.

Further, the moist heat conductive foundation surface, exemplified by but not limited to terry cloth, serves to provide the user of the thermal pack with a comfortable surface for contact with the skin and further to provide the thermal pack with an acceptable appearance whether moisture is applied by the user or not.

In the preferred embodiment, a heat retentive and heat conductive material is disposed within the substantially disk-shaped centrally located conformable member. Such heat retentive and heat conductive material is one of a variety of conventional thermal gel materials or conventional thermal rubber-like flexible solids all of which are well known in the art of medical thermal packs.

The disk-shaped conformable member houses the heat retentive heat conductive gel in a completely enclosed cavity within the conformable member. The disk-shaped conformable member is pliant and flexes from a substantially flat shape when not in use to a substantially cup shape to conform to the breast being covered.

In the alternative, the disk-shaped conformable member may be made from a pliant, gelatinous heat conductive material capable of being cut or molded forming flexible shapes.

The disk-shaped conformable member is preferably constructed of a pliable material provided with an inner cavity to contain the heat retentive heat conductive gel. The disk-shaped conformable member has an inner surface and an outer surface, the inner surface facing toward the user's breast.

The disk-shaped conformable member's inner surface is preferably suitably attached to the moist heat conductive foundation surface, as by stitching, but without limitation to the manner in which attachment is achieved. The moist heat conductive foundation surface is thus disposed adjacent to the disk-shaped conformable member and covers the inner surface thereof to provide a soft and comfortable facing which comes into contact with the skin of the user's breast.

The pliable material of the disk-shaped conformable member may be permeable or impermeable to fluids such as water. Where the thermal gel material selected for a particular embodiment is aqueous in nature or has an aqueous component, it may be desirable to prevent the thermal gel material and/or its aqueous component and/or its liquid component comprised of a liquid other than water from permeating the material of the disk-shaped member and thereby leaking in an undesirable fashion. To prevent such leakage, the pliable material of the disk-shaped conformable member should be a material selected for liquid-impermeability and for resistance to attack by any component or combination of components of the thermal gel housed therein.

In the alternative, it may be desirable to use a thermal gel material for which water is an essential ingredient, and from which water may normally evaporate. There are conventional thermal gels known in the medical thermal pack art which exemplify this water evaporative characteristic.

In such a case, the pliable material of the disk-shaped conformable member may be permeable to fluids such as water. When a substantial amount of water has naturally evaporated from the thermal gel material such water can then be replaced by water soaking the pliable material of the disk-shaped conformable member to restore the lost moisture.

However, it is nonetheless possible to employ a thermal gel material which is normally expected to lose moisture through evaporation by sealing it in an impermeable pliable material of the disk shaped conformable member. In such case, the naturally-contained moisture of the thermal gel would never be lost, because evaporation would be entirely prevented by the impermeability of the pliable material of the disk-shaped conformable member.

When used to heat the breast, the user would warm the heat retentive heat conductive gel within the conformable member any one of a variety of ways. The preferred method is to soak the conformable disk-shaped member in warm water for a few minutes. Such warm water soaking would serve to moisten the moist heat foundation surface as well as to warm the heat retentive heat conductive gel. When the thermal pack of the present invention has been sufficiently warmed, the user would insert it into a conventional brassiere for a period of time, and then remove it for re-warming as desired. Alternatively, the user could manually apply the thermal pack to the breast and hold it in place manually for a desired time period.

When used to cool the breast, the thermal pack of the present invention is cooled, as by refrigeration, until a suitably cool temperature is achieved within the heat retentive heat conductive gel. Application is as above described. When used to cool the breast, the moist heat foundation surface is generally not provided with water, although it could be if rapid and efficient cooling of the breast is desired.

In an alternative embodiment, heating or cooling of the heat retentive heat conducting material may be achieved by a thermochemical reaction, as is well known in the medical thermal pack art. An endothermic or an exothermic chemical reaction can be achieved by mixing two or more ingredients stored in sealed separate compartments until the moment of use. The endo- or exo- thermic nature of the reaction will provide, respectively, cold or heat. Mixing materials such as water and dry solid ammonium nitrate are well known in the thermal pack art to produce an endothermic reaction. Mixing materials such as water and dry solid calcium chloride are also well known in the medical thermal pack art for producing an exothermic reaction. The materials cited here for producing endo- or exo-thermic reactions are merely examples and are not intended to limit the number or kinds of materials useable to produce heat or cold or to limit the scope of the present invention, which scope will be readily understood by those skilled in the medical thermal pack art.

It is contemplated that the use of ingredients stored sealed separate compartments for use in producing heat or cold will comprise a one-use disposable embodiment of the present invention. In contrast, the embodiment in which the present invention is soaked in warm water for heat or refrigerated for cold is a re-useable embodiment.

Where ingredients must be mixed for heat or cold in a one-use embodiment, the ingredients would be stored within the cavity in the conformable disk-shaped member. The user would have means to break the seals of the two or more ingredient compartments, thus allowing mixing of the heat or cold producing ingredients within the cavity of the disk-shaped conforming member. Seal breaking means are exemplified, but not limited to, a manual action of bending or twisting the conformable member so as to break internal compartment seals allowing mixing of the heat-or-cold producing ingredients.

DESCRIPTION OF THE DRAWINGS

FIG. 16 shows the conformable member in a flattened configuration while FIG. 17 shows the conformable member in a flexed, cup-shaped configuration.

FIG. 18 shows the conformable member in a flattened configuration while FIG. 19 shows the conformable member in a flexed, cup-shaped configuration.

DETAILED DESCRIPTION OF THE PREFERRED EMBODIMENT

Figure 1:
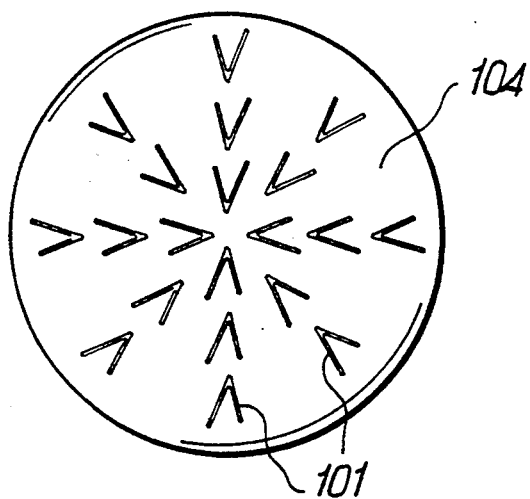
FIG. 1 shows a top view of the outer side of a disk-shaped conformable member having a plurality of L-shaped indentations.

As shown in FIG. 1 the outer side (104) of a disk-shaped conformable member has a plurality of L-shaped indentations (101).

Figure 2:
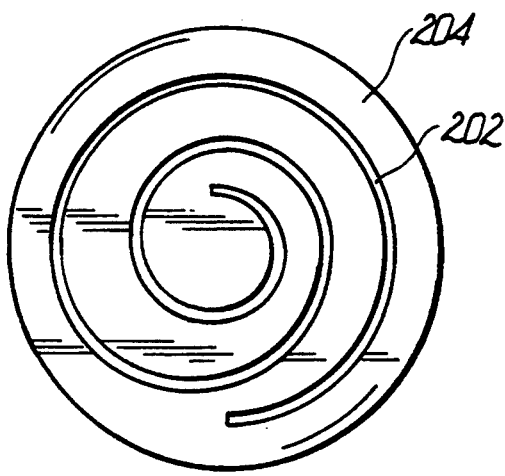
FIG. 2 shows a top view of the outer side of a disk-shaped conformable member having an elongated spiral shaped indentation.

As shown in FIG. 2 the outer side (204) of another disk-shaped conformable member has an elongated spiral shaped indentation (201).

Figure 3:
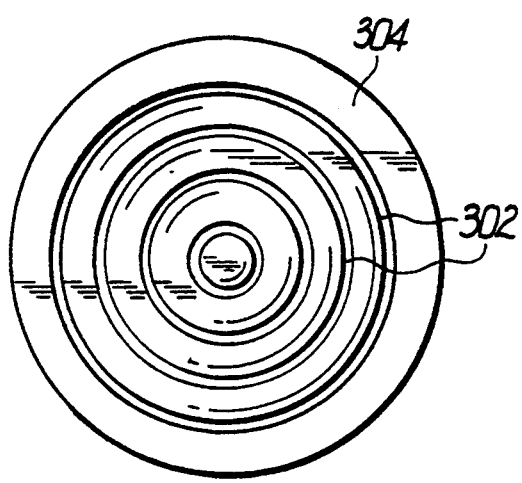
FIG. 3 shows a top view of the outer side of a disk-shaped conformable member having a plurality of substantially concentric circular indentations.

As shown in FIG. 3 the outer side (304) of another disk-shaped conformable member has a plurality of substantially concentric circular indentations (301).

Figure 4:
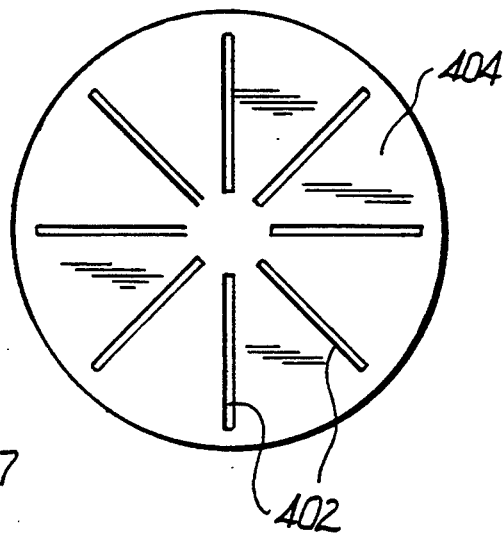
FIG. 4 shows a top view of the outer side of a disk-shaped conformable member having a plurality of substantially straight indentations in a radiating pattern, wherein the indentations comprise radii of the disk-shaped conformable member.

As shown in FIG. 4 the outer side (404) of an alternate disk-shaped conformable member includes a plurality of substantially straight indentations (401) in a radiating pattern, wherein the indentations comprise radii of the disk-shaped conformable member.

Figure 5:
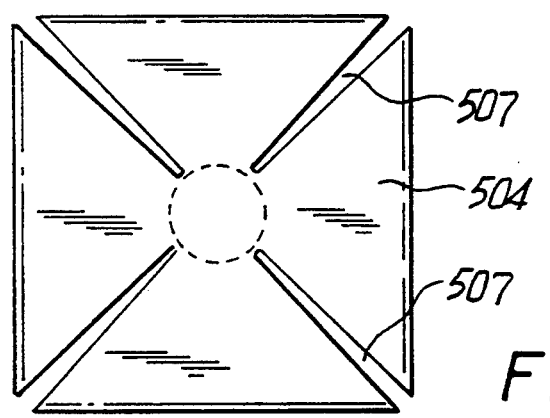
FIG. 5 shows a top view of the outer side of a square-shaped conformable member having a plurality of tapered apertures extending substantially from the center of the member to the edges thereof, the tapered apertures being widest at the edges and narrowest at the center of the conformable member.

As shown in FIG. 5 the outer side (504) of a further square-shaped conformable member has a plurality of tapered apertures (507) extending substantially from the center of the member to the edges thereof, the tapered apertures being widest at the edges and narrowest at the center of the conformable member.

Figure 6:
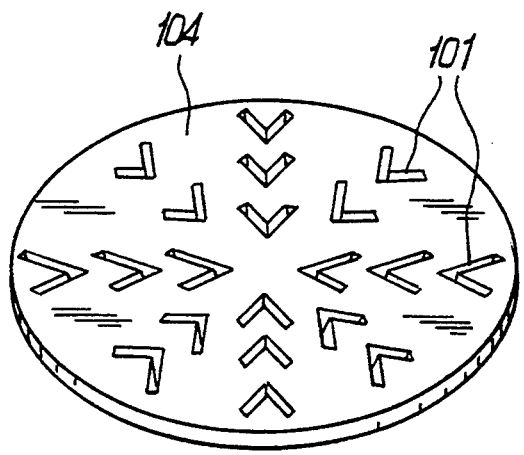
FIG. 6 is a perspective view of a disk-shaped conformable member having a plurality of L-shaped indentations.

As shown in FIG. 6 a further disk-shaped conformable member includes outer side (104) and a plurality of L-shaped indentations (101).

Figure 7:
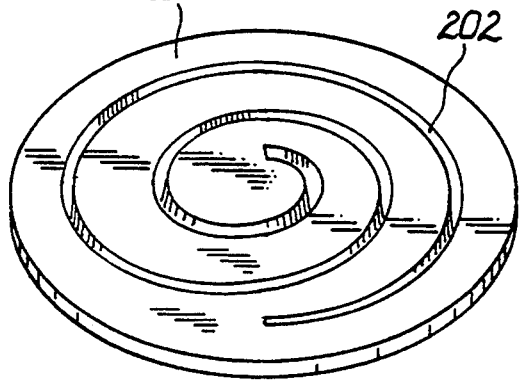
FIG. 7 is a perspective view of the outer side of a disk-shaped conformable member having an elongated spiral shaped indentation.

As shown in FIG. 7 the outer side (204) of another disk-shaped conformable member includes an elongated spiral shaped indentation (201).

Figure 8:
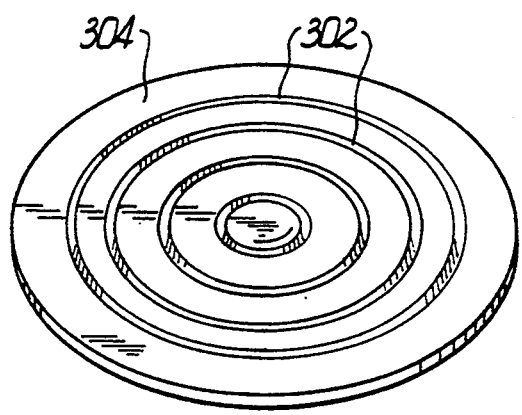
FIG. 8 is a perspective view of the outer side of a disk-shaped conformable member having a plurality of substantially concentric circular indentations.

As shown in FIG. 8 the outer side (304) of another disk-shaped conformable member has a plurality of substantially concentric circular indentations (301).

Figure 9:
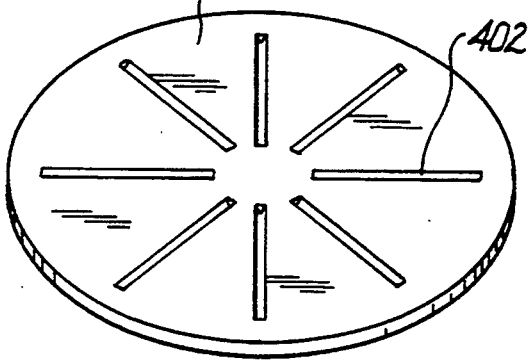
FIG. 9 is a perspective view of the outer side of a disk-shaped conformable member having a plurality of substantially straight indentations in a radiating pattern, wherein the indentations comprise radii of the disk-shaped conformable member.

As shown in FIG. 9 of the outer side (404) of an alternate disk-shaped conformable member has a plurality of substantially straight indentations (401) in a radiating pattern, wherein the indentations comprise radii of the disk-shaped conformable member.

Figure 10:
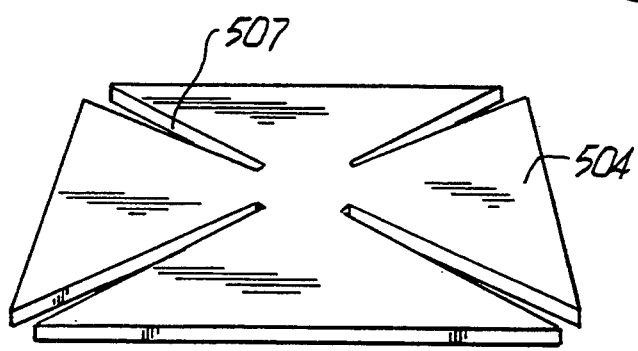
FIG. 10 is a perspective view of the outer side of a square-shaped conformable member having a plurality of tapered apertures extending substantially from the center of the member to the edges thereof, the tapered apertures being widest at the edges and narrowest at the center of the conformable member.

As shown in FIG. 10 of the outer side (504) of an alternate square-shaped conformable member having a plurality of tapered apertures (507) extending substantially from the center of the member to the edges thereof, the tapered apertures being widest at the edges and narrowest at the center of the conformable member.

Figure 11:
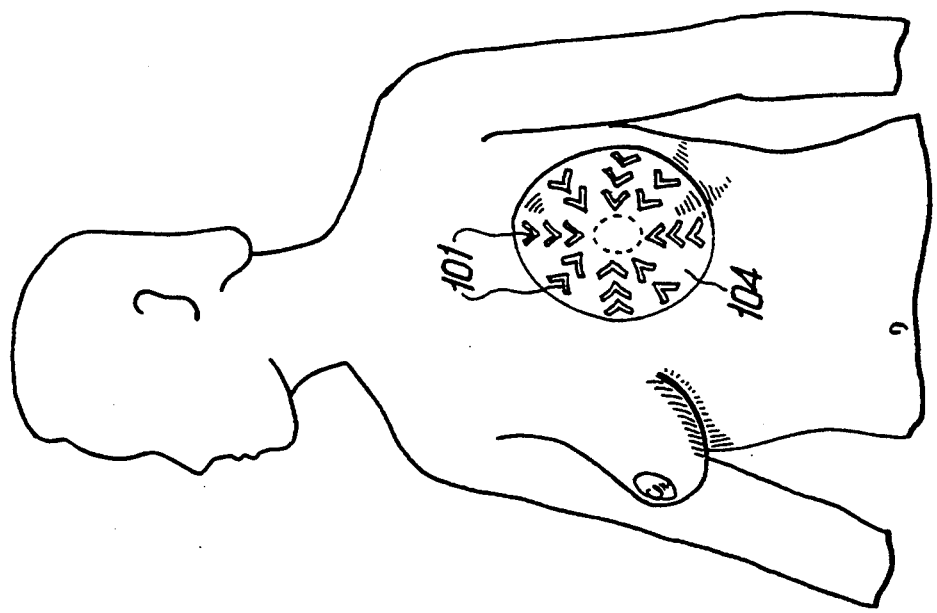
FIG. 11 is a perspective view of a disk-shaped conformable member having a plurality of L-shaped indentations in place upon a female breast.

As shown in FIG. 11 of the outer side (104) a disk-shaped conformable member of FIG. 6 has a plurality of L-shaped indentations (101) in place upon a female breast.

Figure 12:
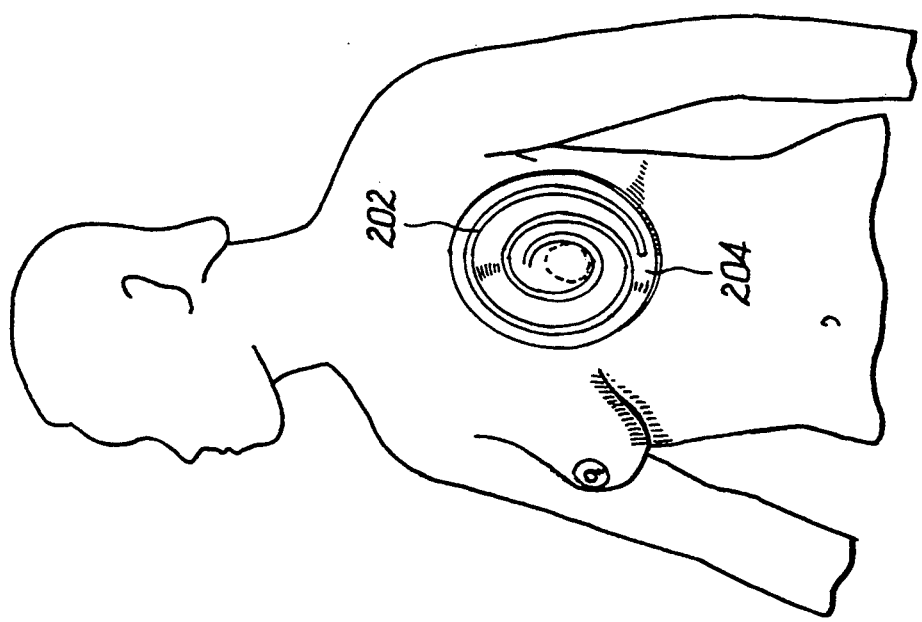
FIG. 12 is a perspective view of the outer side of a disk-shaped conformable member having an elongated spiral shaped indentation in place upon a female breast.

As shown in FIG. 12 of the outer side (204) of a disk-shaped conformable member as in FIG. 2 having an elongated spiral shaped indentation (201) in place upon a female breast.

Figure 13:
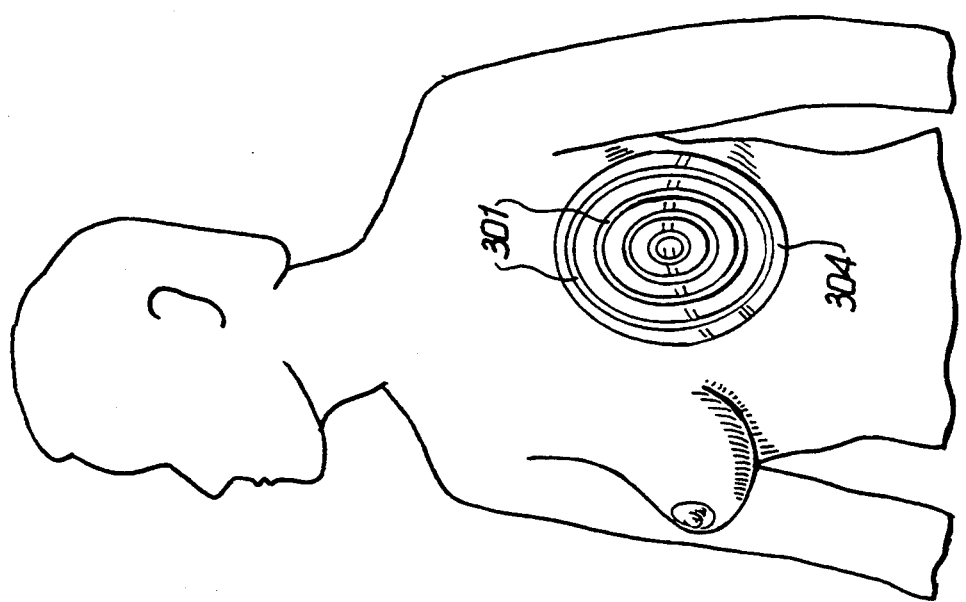
FIG. 13 is a perspective view of the outer side of a disk-shaped conformable member having a plurality of substantially concentric circular indentations in place upon a female breast.

As shown in FIG. 13 of the outer side (304) of a disk-shaped conformable member as in FIG. 3 has a plurality of substantially concentric circular indentations (301) in place upon a female breast.

Figure 14:
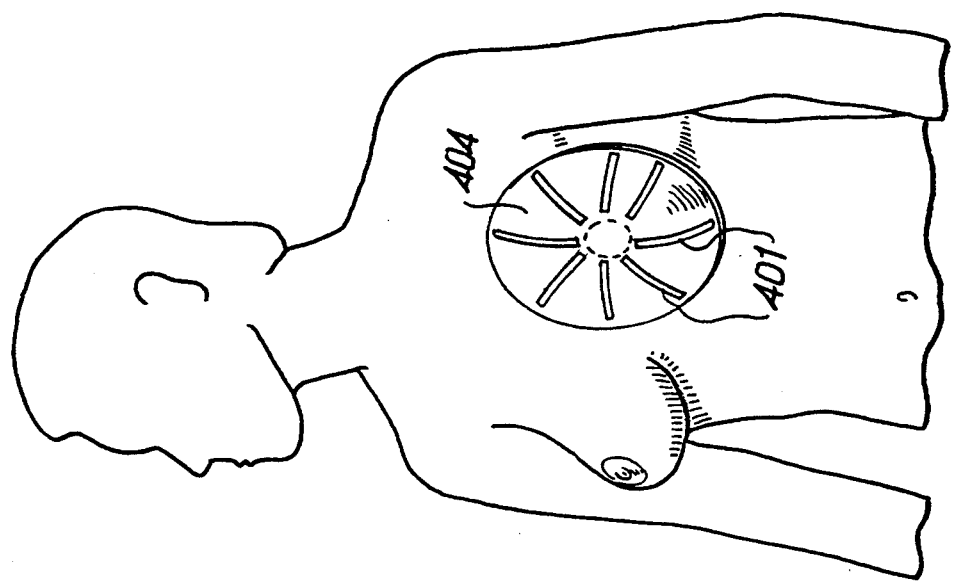
FIG. 14 is a perspective view of the outer side of a disk-shaped conformable member having a plurality of substantially straight indentations in a radiating pattern, wherein the indentations comprise radii of the disk-shaped conformable member, the disk being shown in place upon a female breast.

As shown in FIG. 14 of the outer side (404) of a disk-shaped conformable member as in FIG. 4 has a plurality of substantially straight indentations (401) in a radiating pattern, wherein the indentations comprise radii of the disk-shaped conformable member, the disk being shown in place upon a female breast.

Figure 15:
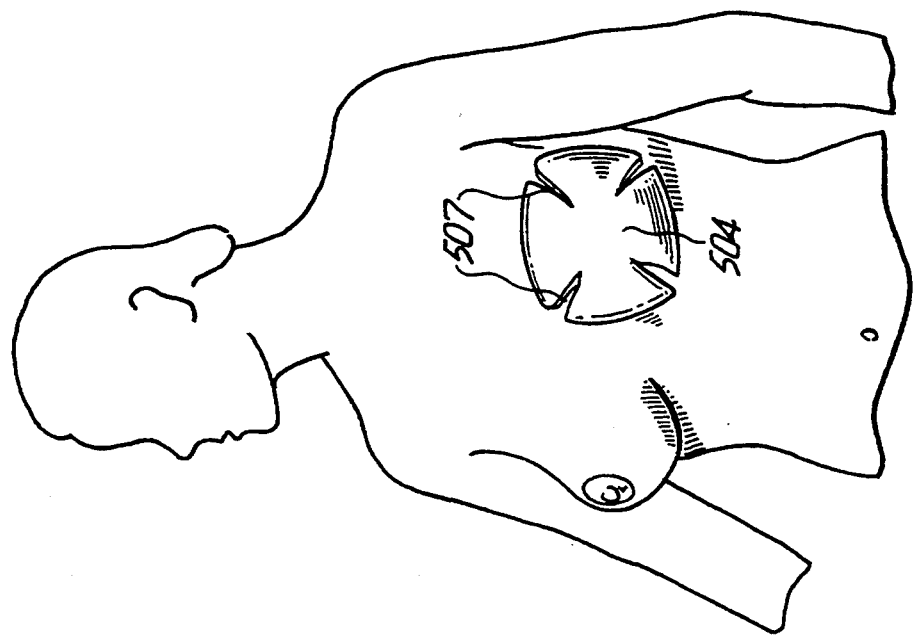
FIG. 15 is a perspective view of the outer side of a square-shaped conformable member having a plurality of tapered apertures extending substantially from the center of the member to the edges thereof, the tapered apertures being widest at the edges and narrowest at the center of the conformable member, the square shaped member being shown in place upon a female breast.
Figure 21:
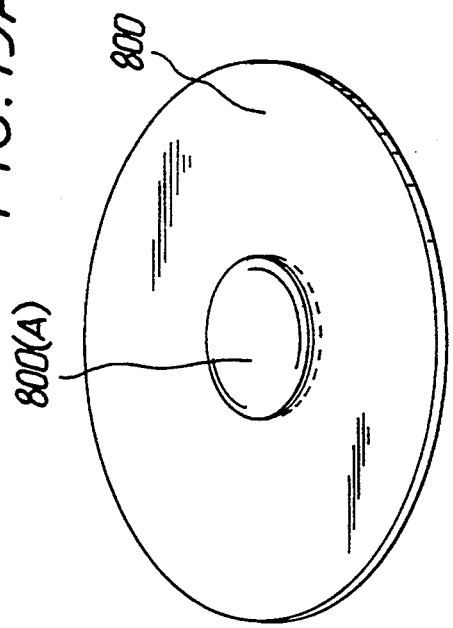
FIGS. 21, 21A, 21B, 21C are perspective, top plan and closeup views of a nipple shield within a circular, heat-cold pack conforming disk.

As shown in FIG. 15 of the outer side (504) of a square-shaped conformable member as in FIG. 5 has a plurality of tapered apertures (507) extending substantially from the center of the member to the edges thereof, the tapered apertures being widest at the edges and narrowest at the center of the conformable member, the square shaped member being shown in place upon a female breast.

Figure 16:
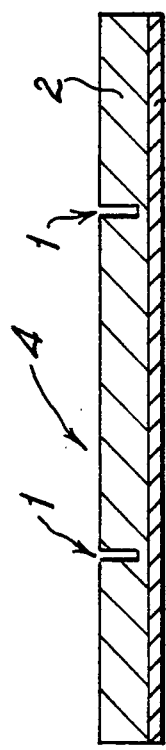
FIGS. 16 and 17 are cross sections of a conformable disk showing indentations, heat retaining gel cavity, inner side of the conformable member having moist heat conductive foundation surface, outer side, and inner side attached to and disposed adjacent to conductive foundation surface.
Figure 17:
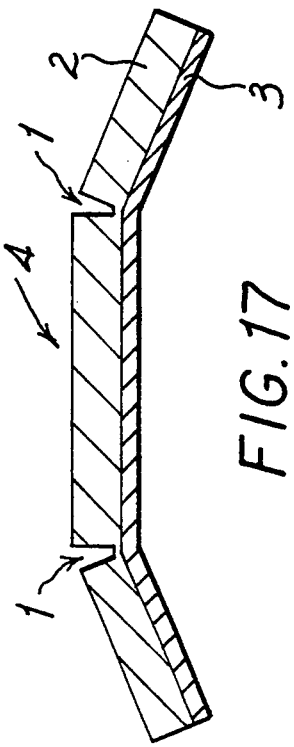

As shown in FIGS. 16 and 17 a conformable disk includes indentations (1), heat retaining gel cavity (2), the inner side of the conformable member having moist heat conductive foundation surface (3), outer side (4), and inner side (5) attached to and disposed adjacent to conductive foundation surface (3). As shown in FIG. 16 the conformable member may have a flattened configuration while as shown in FIG. 17 the conformable member may have a flexed, cup-shaped configuration.

Figure 18:
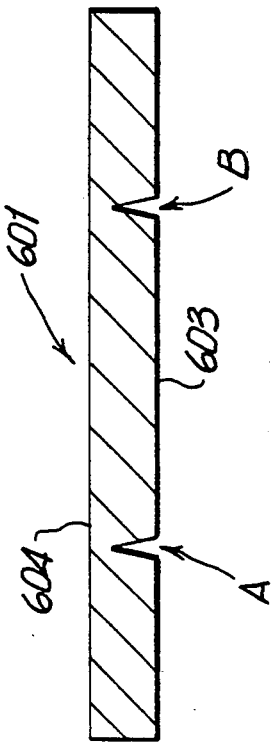
FIGS. 18 and 19 are cross sections of a conformable disk of a pliant heat retaining cutable material showing indentations, an inner side and an outer side.
Figure 19A:
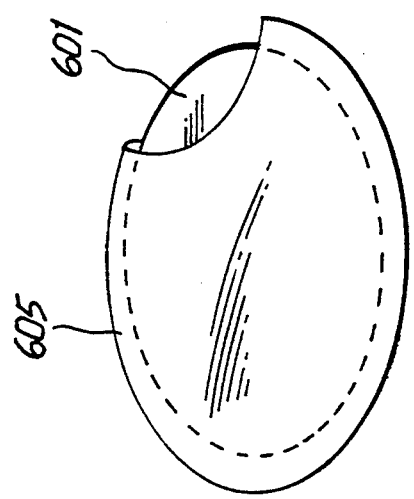
Figure 19:
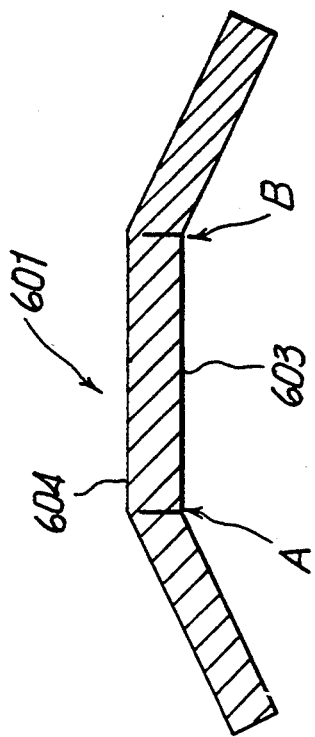

As shown in FIGS. 18 and 19 a conformable disk 601 of a pliant heat retaining, cutable or moldable material 602, includes indentations A and B, an inner side 603, and outer side 604, wherein the indentations A & B are indented into the inner side 603 of disk 601.

It assumed that the indentations A and B can also be indented in a reverse orientation, that is, into the outer side 604 of disk 601, similar to the orientation of the indentations shown in FIGS. 16 and 17. The disk 601 may be optionally insertable within a conventional moist heat conductive ferrule sheath, such as made of terry cloth.

Figure 20:
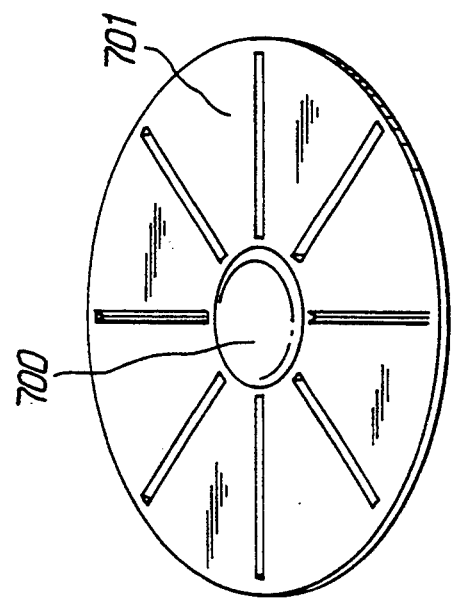
FIG. 20 is a perspective view of a disk with nipple shield.
Figure 21A:
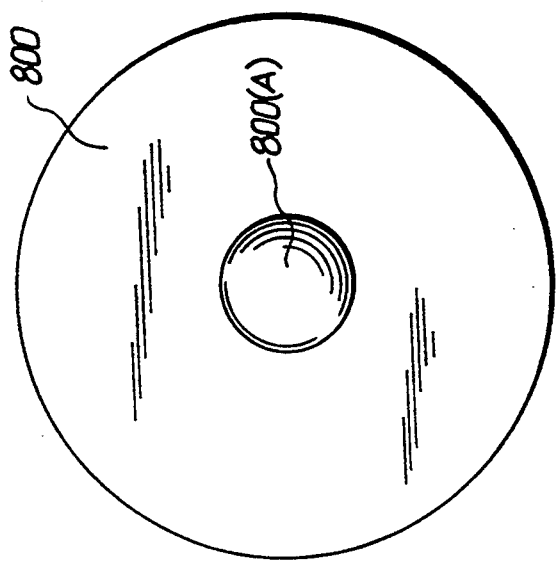
Figure 21C:
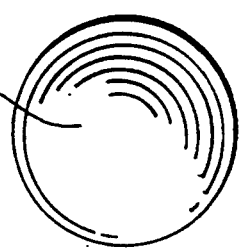
Figure 21B:
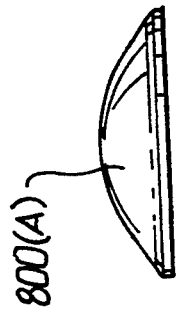

Various design modifications may be made to isolate the nipple from the direct application of heat or cold. As shown in FIG. 20, there is shown a centrally located nipple 700 shield within the conforming member disk 701.

As shown in FIGS. 21, 21A, 21B, 21C a nipple shield 800 (A) is provided within a circular, heat-cold pack conforming disk 800.

It is further assumed that other modifications may be made to the present invention, without departing from the spirit and scope of the appended claims.

We claim:

1. A thermal heat pack adapted to closely correspond to the contours of various sized female breasts to heat the adjacent skin area; said thermal heat pack comprising:

a sealed generally flattened conforming member;

a bottom foundation member forming one side of said thermal heat pack;

said flattened conforming member including a plurality of radially extending geometrically extending portions radiating from a common central portion within said flattened conforming member;

said conforming member including pliant heat conducting material, said heat pack bendable over said breast, such that said bottom foundation member is removably adjacent to said breast, thus permitting uniform application of heat to said breast, wherein said conforming member further comprises a plurality of radially extending indentations, said conforming member includes an outer wall extending about an exterior edge of said conforming member of said heat pack; and said heat pack defining a fluid flow chamber therebetween; said chamber including a plurality of segmented recesses positioned within said heat pack for the circulation of the said pliant heat conducting material within said heat pack.

2. The thermal heat pack of claim 1 wherein said conforming member includes said bottom foundation membering being mounted to said conforming member.

3. The thermal heat pack of claim 1 wherein said thermal heat pack further comprises said foundation member being mounted to conforming member to form a container therebetween for the circulation of the second heat conductive material;

said portions being interconnected such that said fluid traverses substantially the entire interior area of said heat pack.

4. The thermal heat pack as in claim 1 wherein said heat conductive material is a heat imparting medium.

5. The thermal heat pack as in claim 1 wherein said heat conductive material is a cooling medium.

6. The thermal heat pack as in claim 1 further comprising a central nipple portion bearing a circular shape.

7. The thermal heat pack of claim 1 wherein said conforming member is comprised of a liquid-impermeable material.

8. The thermal heat pack of claim 1 wherein said conforming member is comprised of a liquid permeable material.

9. The thermal heat pack of claim 1 wherein a. said thermal heat pack is provided with a plurality of materials sealed in separate compartments within said heat pack, the separate compartments being provided with manually breakable seals thereon; and further wherein b. said manually breakable seals communicating with said at least one cavity for releasing said plurality of materials to freely mix within said at least one cavity.

10. The thermal heat pack of claim 9 wherein the free mixing of said plurality of materials results in an endothermic chemical reaction.

11. The thermal heat pack of claim 9 wherein the free mixing of said plurality of materials results in an exothermic chemical reaction.

12. The thermal heat pack of claim 1, wherein said indentation is comprised of a plurality of substantially L-shaped indentations substantially evenly distributed over the outer side of said shaped conformable member, and being substantially equidistantly distributed thereupon.

13. The thermal heat pack of claim 1, wherein said indentation is comprised of a plurality of curves constituting an elongated indentation with a substantially spiral shape.

14. The thermal heat pack of claim 1, wherein said indentation is comprised of a plurality of substantially concentric circular indentations.

15. The thermal heat pack of claim 1, wherein said indentation is comprised of a plurality of substantially straight indentations, the straight indentations extending radially in a direction substantially from the center of the conforming member to the perimeter thereof.

16. The thermal heat pack of claim 1 wherein the conforming member is substantially square in shape, the conforming member having tapered apertures extending from about the center of the conforming member to the corners of the substantially square shape.

17. A thermal pack for application to a protruding body for therapeutic application of heat or cold to the body part part, the thermal pack being adjustable for varying body part sizes; and the thermal pack further being substantially flat when not in use; and further being conformable to the contours of the protruding body part when in use, said thermal pack comprising:

a sealed generally flattened conforming member having a thickness with at least one sealed cavity disposed therein; said conforming member having a circumferential perimeter edge;

the conforming member having an inner side and an outer side, the inner side facing the skin of the protruding body part when the thermal pack is in use;

the conforming member being made of a suitably pliable heat conductive bendable material; and further wherein the conforming member having radially extending indentations in said conforming member to permit said conforming member to assume a substantially conforming cup shape when applied to a protruding body part; and further wherein said inner side of said conforming member having a moist heat conductive foundation surface suitably attached to said inner side, the moist heat conductive foundation surface forming a layer disposed adjacent to the inner side of said conforming member;

said at least one sealed cavity disposed within the conforming member containing means for retaining and conducting heat; and said at least one sealed cavity disposed within the conforming member containing means for retaining and conducting cold, wherein:

the means for retaining and conducting heat and cold is a thermal gel, said gel being flexible for permitting the conforming member to flexibly change shape to conform to the contours of the protruding body part; and further wherein said gel is in contact with said conforming member;

said gel is substantially evenly distributed throughout said at least one sealed cavity;

said moist heat conductive foundation surface being comprised of a material suitable for contact with human skin;

said selectively positioned indentations in said conforming member being disposed so as to project radially from a central portion of said conforming member in a direction substantially toward the outer, perimeter edge of said conforming member; and, said indentations being a plurality of indentations, said indentations being substantially evenly distributed over said conformable member.

* * * * *